United States Patent [19]

Lübbers et al.

[11] 4,217,194

[45] Aug. 12, 1980

[54] INSTRUMENT FOR POLAROGRAPHIC POTENTIOMETRIC, THERMAL AND LIKE MEASUREMENTS AND A METHOD OF MAKING THE SAME

[75] Inventors: Dietrich W. Lübbers; Horst Baumgärtl, both of Dortmund, Fed. Rep. of Germany; Yukio Saito, Tokyo, Japan

[73] Assignee: Max-Planck-Gesellschaft zur Förderung der Wissenschaften e.V., Göttingen, Fed. Rep. of Germany

[21] Appl. No.: 746,328

[22] Filed: Dec. 1, 1976

[30] Foreign Application Priority Data

Dec. 29, 1975 [DE] Fed. Rep. of Germany ....... 2558947

[51] Int. Cl.² .......................... C23C 15/00; G01N 27/36
[52] U.S. Cl. .......................... 204/192 SP; 204/195 G
[58] Field of Search .......... 204/195 G, 192 C, 192 SP

[56] References Cited

U.S. PATENT DOCUMENTS

| | | | |
|---|---|---|---|
| 2,563,062 | 8/1951 | Perley | 204/195 G |
| 3,314,873 | 4/1967 | Lunsford | 204/192 R |
| 3,476,672 | 11/1969 | Snyder et al. | 204/195 G |
| 3,619,402 | 11/1971 | Wurm et al. | 204/192 R |
| 3,880,737 | 4/1975 | Brunt | 204/195 G |
| 3,959,107 | 5/1976 | Horner et al. | 204/195 G |

OTHER PUBLICATIONS

Saito, "J. Appl. Phys.," 1967, pp. 979–983.
Bicher et al., "J. Appl. Phys.," 1970, pp. 387–390.

*Primary Examiner*—John H. Mack
*Assistant Examiner*—William Leader
*Attorney, Agent, or Firm*—Michael J. Striker

[57] ABSTRACT

A probe having a measuring device for polarographic, potentiometric, thermal and like measurements has a high-resistance transducer which is provided with leads. A body of insulating material is arranged about the transducer and a metal-containing body is arranged about the insulating material. The metal-containing body includes a metal layer which is essentially free of pores and essentially impervious to the diffusion of liquid therethrough and which thus seals the insulating material against contamination by foreign matter. A metal layer which is essentially free of pores and essentially impervious to the diffusion of liquid therethrough may be formed by sputtering the metal onto a substrate using a high-frequency field at an output of 10 to 40 watts per square centimeter of target surface, the sputtering operation being carried out for a period of 5 to 10 minutes in an Ar atmosphere having a pressure of $8 \times 10^{-4}$ torr. An insulating layer may be formed by sputtering an insulating material onto a substrate using a high-frequency field and an atmosphere made up of a protective gas and a reactive gas having partial pressures such that the total pressure of the atmosphere is $8 \times 10^{-4}$ torr.

59 Claims, 16 Drawing Figures

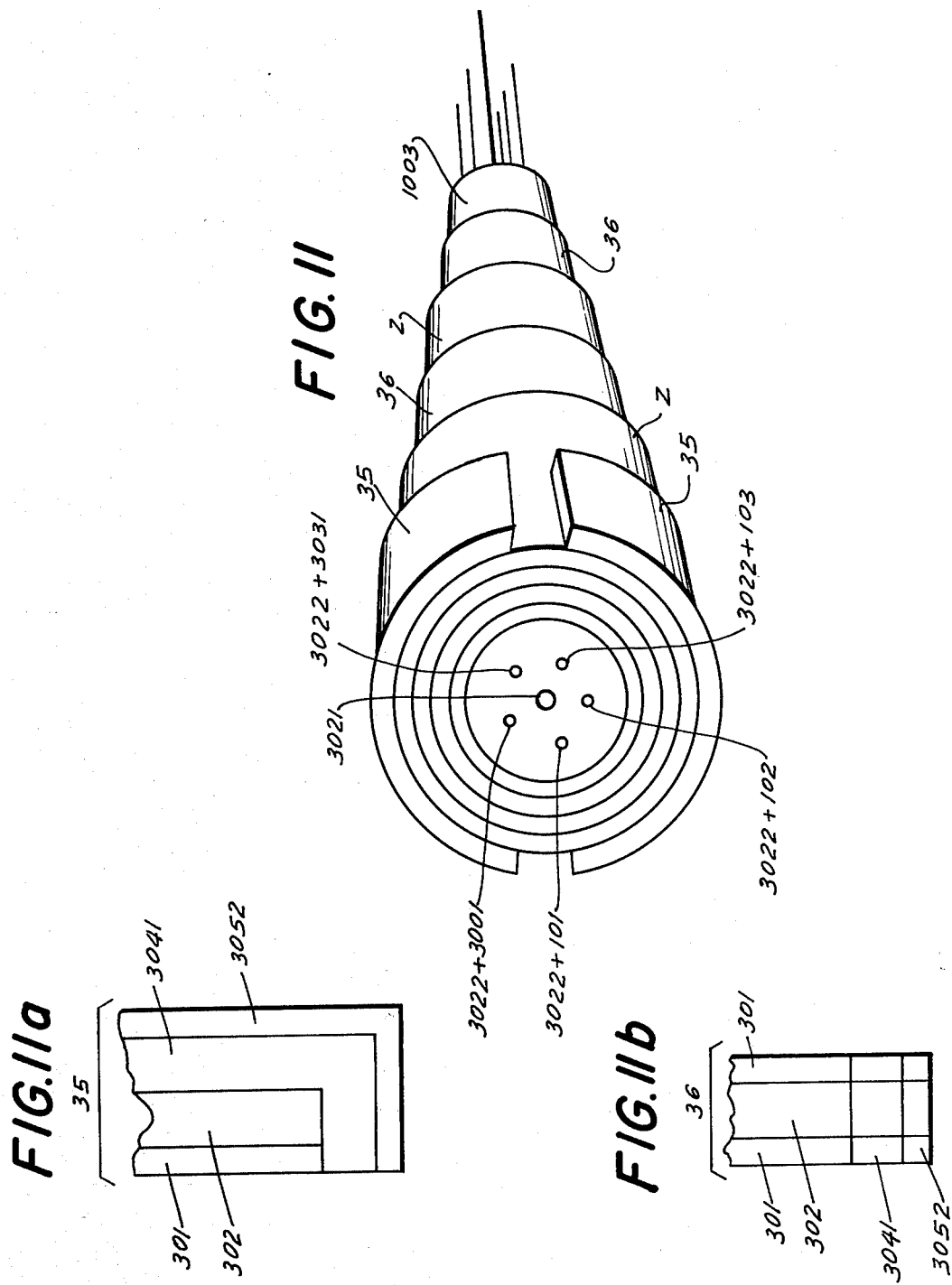

INSTRUMENT FOR POLAROGRAPHIC POTENIOMETRIC, THERMAL AND LIKE MEASUREMENTS AND A METHOD OF MAKING THE SAME

BACKGROUND OF THE INVENTION

The invention relates to a measuring device of the type having a transducer, and especially a measuring device of the type having a high-resistance transducer which is provided with electrical leads.

Measuring devices of the type outlined above are used for polarographic measurements such as the determination of the partial pressures of oxygen and hydrogen in fluids. Such measuring devices are also used for potentiometric measurements such as the determination of pH values as well as for the measurement of ionic activities and thermal values such as heat flow. Measuring devices of the type outlined above are further used for temperature and pressure measurements.

Such devices may be constructed as macroprobes or microprobes. When using a measuring device of the above type, and particularly in those cases where the measuring device is constructed as a microprobe, it is frequently necessary to sharply delimitate the field of measurement. In such an event, the measuring device must have a small, well-defined working surface.

Measuring devices of the type outlined above are of particular utility for measurements in biological systems, e.g. for measurements involving blood, skin tissue and even individual cells. Stringent requirements are imposed on the mechanical stability of the measuring devices, especially for the last-mentioned application, since otherwise the required manipulations would not be possible in the microregion. However, although stringent requirements are imposed on the mechanical stability of the measuring devices, even more stringent requirements are imposed on the electrical characteristics of the measuring devices and the constancy of these characteristics.

In order to satisfy these requirements, attempts have been made to make the transducer, its leads and its insulation in the form of thin films or layers by means of vapor phase deposition, rolling, electrolytic deposition and direct current sputtering (Saito, J. Appl. Phys., 1967/979; Bicher, J. Appl. Phys., 1970/387; Naturwissenschaften, 1974/12, page 660; German Auslegeschrift 1,598,988).

These known films have certain disadvantages, however. Thus, due to the porosity of the insulating and metallic layers, the insulating properties undergo chemical- or physicochemical-induced changes since, for example, foreign matter diffuses into the layers or hydration takes place at the insulating layer. The prior art methods do not result in the requisite pore-free layers. Consequently, the electrical characteristics either cannot be achieved or undergo change during use.

Of the changes in electrical characteristics, those which occur in the electrical resistivity of the insulating layer are of particular significance. This is especially important where high-resistance transducers, that is, transducers having an internal resistance of 1 Megohm and more, are concerned, inasmuch as the variations in resistivity become fully effective here.

The changes in resistivity affect the measurement signal. However, it is not only the measurement signal which is adversely affected by the changes in resistivity. Thus, the changed resistivity also alters the field of measurement because additional portions of the electrode and lead surfaces, namely, those located beneath the insulation layer, can now interact with the object or substance which is to be subjected to a measurement. Accordingly, the field of measurement is less sharply defined than it was prior to the decrease in resistivity.

SUMMARY OF THE INVENTION

One object of the invention is to provide a measuring device which enables changes in resistivity of the insulating layer to be avoided, at least to a great extent.

Another object of the invention is to provide a method of making such a measuring device and, more particularly, to provide a method of forming a metal layer and a method of forming an insulating layer.

These objects, as well as others which will become apparent as the description proceeds, are achieved in accordance with the invention.

According to the invention, there is provided a measuring device which includes a transducer, a body of insulating material arranged about the transducer and a metal-containing body arranged about the insulating material. The metal-containing body comprises at least one substantially closed metal layer deposited on the body of insulating material by sputtering.

As a result, the metal layer is substantially free of pores and substantially impervious to the diffusion of liquid therethrough thereby sealing the insulating material against contamination by foreign matter.

Another aspect of the invention relates to a method of forming a layer of metal on a substrate wherein the metal is sputtered onto the substrate using a high-frequency field and an atmosphere having an Ar pressure of about $8 \times 10^{-4}$ torr.

Advantageously, the total pressure of the atmosphere is $8 \times 10^{-4}$ torr.

Yet another aspect of the invention relates to a method of forming a layer of insulating material on a substrate wherein the insulating material is deposited on the substrate in an atmosphere which includes protective gas and reactive gas having partial pressures such that the sum thereof is of the order of $8 \times 10^{-4}$ torr.

Advantageously, the total pressure in the latter atmosphere is $8 \times 10^{-4}$ torr.

The deposition of the insulating material on the substrate preferably involves sputtering.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 11 schematically illustrates the construction of a macroprobe having a multiple-electrode configuration;

FIG. 11a represents an enlarged view of one of the coats provided on the macroprobe of FIG. 11; and FIG. 11b represents an enlarged view of another of the coats provided on the macroprobe of FIG. 11.

DESCRIPTION OF THE PREFERRED EMBODIMENTS

Figure 1:
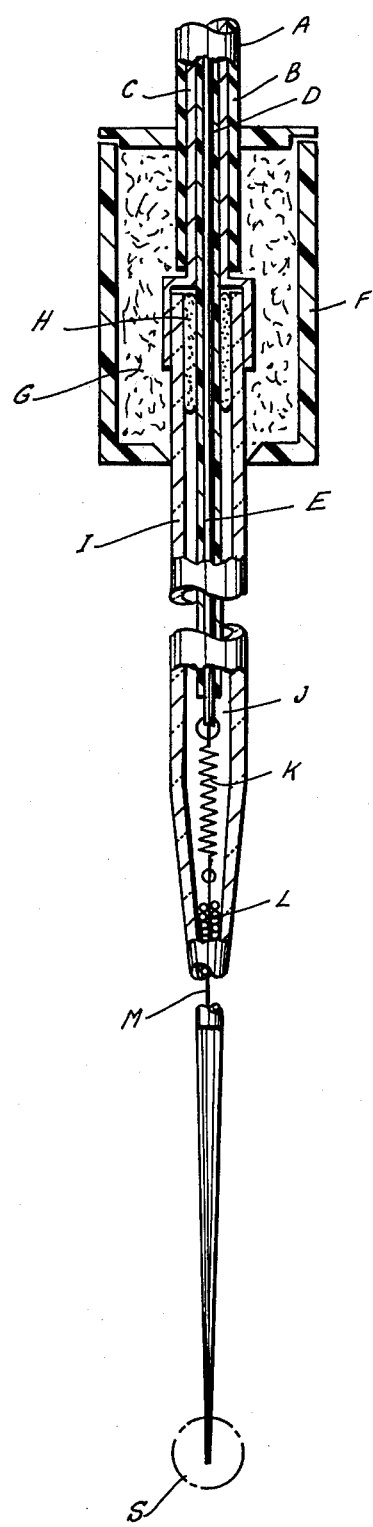
FIG. 1 is a sectional view schematically illustrating the construction of a microprobe for the measurement of ionic activities.

In a preferred aspect, the invention relates to a measuring device of the type having a high-resistance transducer which is provided with electrical leads.

In order to protect against reductions in the resistivity of the insulation, the invention proposes to seal an insulating layer of the device with at least one diffusion-tight, closed metal layer.

The metal layer is favorably deposited in such a manner that a closed, substantially pore-free coating is obtained. This coating acts as a diffusion barrier for fluid media and thus plugs up, that is, "seals," pores and microcracks in the insulating layer. This results in the advantage that a time-dependent reduction in the electrical resistivity of the insulating layer no longer occurs.

The metal layer is advantageously sputtered onto the insulating layer in a high-frequency field since the requisite compactness and imperviousness of the metal layer is achievable by means of such a procedure.

For applications where the presence of metal may provide a disturbing influence, or in cases where particularly stable insulating layers are required, the metal layer may be arranged intermediate two insulating layers.

In addition to its use in providing a sealing surface, the metal layer may simultaneously serve as an electrode or as a screen or shield.

In order to achieve good adherence of the metal on oxidic substrates, it is advantageous to use Ta for the metal layer.

For the sake of simplifying the description of various embodiments of the invention, the following conventions will be adopted in the specification and claims:

The measuring surfaces of the measuring devices will be considered as being generated by the taking of a section through the substrate and the layers in a plane normal to the plane of the layers or in a plane which is inclined to the planes of the layers.

Furthermore, for cylindrical measuring devices or electrodes, layers which follow one another in radial direction will be separated by a "—" and the order of the layers will be in radially outward direction, that is, in a direction outwardly from the cylinder axis. Layers which follow one another in axial direction will be separated by a "+" and the layer following the "+" will be located nearer the measuring surface than the preceding layer, that is, the layer before the "+". Layers which follow one another in tangential direction will be separated by a ";". Layers which cooperate with one another will be enclosed by brackets.

In addition, the letter "U" will be used to represent a metal-containing body which includes a layer of metal. The latter "U" may represent a single layer or a body having a multilayered configuration.

The letter "Z" will be used to represent a body of insulating material. The letter "Z" may represent a single layer or a body having a multilayered configuration.

It is to be noted that the term "glass" will be used in the specification and claims in addition to terms such as "insulating material" and "insulator". This is done merely for the sake of description and is not intended to imply that terms such as "insulating material" and "insulator" do not encompass glass.

With the foregoing in mind, it is now pointed out that one embodiment of the invention contemplates a metal-containing body having a plurality of metal layers, that is, $U=(U_1-U_2-U_3- \ldots)$ where $U_1, U_2, \ldots$ represent different metals. This construction may be referred to as a metal packet. With such metal packets, it is possible to satisfy the different requirements which arise in different instances as regards the coefficients of expansion, the adhesive strengths and the metal properties themselves.

A metal-containing body having the configuration (Ta—Pt—Au—Pt—Ta) is particularly well-suited as a working electrode. With such a working electrode, it becomes possible, for example, to generate gas in the measuring region by electrolysis.

The configuration (Ta—Pt—Ag—AgCl) is well-suited as a reference electrode. Here, it is preferred for the Ta layer to lie adjacent the insulating layer.

A metal-containing body of the configuration (Ta—Pt—Ta)+(Pd) is particularly well-suited for the measurement of hydrogen.

In addition, the configuration (Ta—Pt—Ta), which may be used as a screen or working electrode, is readily manufactured and can be used for a wide variety of applications.

A metal-containing body having the configuration {[(Ta—Pt—Ta)+(Ag)]—[AgCl]}+{AgCl} is particularly well-suited as a reference electrode for measurements with a side face and a front or end face.

A metal-containing body having the configuration [Ta—Pt—Ta]+[(Ag)+(AgCl)] is contemplated for measurements with a front or end face.

According to a further embodiment of the invention, an intermediate or transition body, or intermediate or transition bodies, are arranged between the metal layer and the insulating layer. An advantage of this construction resides in that a better adjustment to the temperature coefficients and a further increase in the forces of adhesion may be achieved by appropriate adjustment of the structures of the materials.

Particularly advantageous for this purpose when a metal layer of Ta is involved is an intermediate body having the configuration ($Ta_2N$—$Ta_2O_5$). Here, the $Ta_2O_5$ layer is favorably arranged adjacent the Ta layer.

A particularly well-suited insulating body has the configuration ($Al_2O_3$—$Si_3N_4$—$SiO_2$).

In accordance with another embodiment of the invention this insulating body is arranged between two intermediate bodies so as to form an insulating packet. When the intermediate bodies are each constituted by a $Ta_2N$ layer and a $Ta_2O_5$ layer, the insulating packet Z has the configuration Z=($Ta_2O_5$—$Ta_2N$—$Al_2O_3$—$Si_3N_4$—$SiO_2$—$Ta_2N$—$Ta_2O_5$).

Still another embodiment of the invention contemplates for the metal layer to be arranged between two insulating packets so as to obtain a sealing packet having the configuration Z—U—Z. Such a sealing packet may be used with advantage in those cases where particularly aggressive fluids are present or where the presence of a metal must be avoided.

An additional reduction in the influence of water is made possible by covering the measuring device with a hydrophobic layer. However, a working electrode which may be present should remain exposed, that is, should be at most partially covered by the hydrophobic layer. A particularly easily manufactured and stable layer of this type is composed of a polytitanosiloxane.

The bodies and layers described to this point are well-suited for the production of highly stable measuring devices or probes and may be adapted for any special measuring problem by making small changes in the composition and/or construction thereof.

The insulating bodies and layers according to the invention have a high resistance which remains stable in biological media. It is particularly because of this high and stable resistance that it now becomes possible to provide a measuring device with a plurality of transducers or with additional working electrodes so as to obtain a multiple-electrode configuration.

Accordingly, a further embodiment of the invention resides in that additional high-resistance transducers are arranged in the measuring device, the transducers being separated from one another by insulating packets. With such a measuring device, it becomes possible to determine various essential metabolic values simultaneously and to perform such determinations for entities down to single-cell size.

When working electrodes are additionally arranged in the measuring device, it is also possible to measure flux values. For example, $O_2$ or $H_2$ may be generated with a suitable working electrode and the clearance of these gases measured with the measuring electrode which is provided.

According to one embodiment of the invention, a measuring device is provided which is capable of undertaking polarography and the measurement of ions simultaneously. Here, a plurality of bodies are arranged on a glass electrode and beneath a gas-permeable membrane in the configuration [Z—U—Z—U—Z—U]. A preferred form of this arrangement resides in the configuration [(Z—U—Z)—(Ta—Pt—Au—Pt—Ta—Z—(Ta—Pt—Ag—AgCl)].

Another embodiment of the invention proposes a measuring device which is capable of undertaking the measurement of ions and $H_2$ clearance simultaneously with the generation of $H_2$. Here, a plurality of bodies are arranged on a glass electrode and beneath a gas-permeable membrane in the configuration Z—U—{Z—U—Z—U}. A preferred form of this arrangement resides in the arrangement Z—(Ta—Pt—Ta)—{Z—[(Ta—Pt—Ta)+(Pd)]—Z—[Ta—Pt—Ag—AgCl]} with the glass electrode being composed of ion-sensitive glass.

In accordance with an additional embodiment of the invention there is provided a measuring device which is suitable for the punctiform or quasipunctiform measurement of ions and $H_2$. Here, a Pt wire is embedded in glass and a plurality of bodies are arranged on the glass-embedded Pt wire and beneath a gas-permeable membrane so as to obtain the configuration Pt wire-Glass-{U—Z—U—Z}. In a preferred form of this arrangement, the glass in which the Pt wire is embedded is lead glass and the Pt wire is fused into the glass. A preferred configuration contemplated is Pt wire-Lead Glass-{[(Ta—Pt—Ta)+(Pd)]—Z—[Ta—Pt—Au—Pt—Ta]—Z}.

Still another embodiment of the invention proposes a measuring device which is capable of measuring ions, $H_2$ and $O_2$ simultaneously with the generation of $H_2$. Here, five Pt wires are embedded in glass and a plurality of bodies are arranged on the glass-embedded Pt wires in the configuration $$\{U\text{-}Z\text{-}U\text{-}Z\text{-}(U;Z;U)\} + \{\text{membrane}\}.$$

In a preferred form of this arrangement, the glass in which the Pt wires are embedded is lead-free, highly insulating glass and the Pt wires are provided with a covering of ion-sensitive glass and are fused into the lead-free, highly insulating glass. A preferred configuration of the bodies arranged on the glass-embdedded Pt wires is $$\{\{[Ta\text{-}Pt\text{-}Ta] + [(Ag) + (AgCL)]\} - Z - \\ -\{[Ta\text{-}Pt\text{-}Ta] + [(Ag) + (agCl)]\} - Z - (\{[(Ta\text{-}Pt\text{-}Ta) + (Ag)] - \\ [AgCl]\} + \{AgCl\}; Z; \{[(Ta\text{-}Pt\text{-}Ta) + \\ (Ag)] - [AgCl]\} + \{AgCl\})\} + \{\text{membrane}\}.$$

It is also possible to use wires of other metals which are capable of being fused into glass.

A further embodiment of the invention proposes a measuring device which is capable of performing measurements in small, cylindrical measuring zones. Here, a plurality of bodies are arranged on a glass capillary in the configuration (U)+(ion-sensitive layer)−Z. The glass capillary is provided with an opening and is filled with an electrolyte. A reference electrode is arranged in the electrolyte. The opening in the glass capillary is adapted to face the object or substance which is to be subjected to a measurement. It is preferred for the glass capillary to be composed of lead glass.

Yet another embodiment of the invention contemplates a special measuring device for the polarographic determination of the partial pressure of a gas, particularly of the partial pressure of $O_2$ in aqueous solution, especially in biological media. This embodiment of the measuring device includes a membrane which protects the working surface against contamination in known manner. The measuring device is provided with an insulating substrate or carrier as well as an insulating body which is constructed of a plurality of thin films of different insulating materials arranged in sandwich-like fashion and in an alternating array. The measuring electrode is here in the form of a thin film composed of noble metal or of a metallic alloy having noble metal properties and is arranged intermediate the insulating substrate and the sandwich-like insulating body. The working surface is in the form of a surface which is obtained by taking a section through the thin film measuring electrode with a measuring surface arranged normal to the plane of the measuring electrode, that is, the working surface is in the form of a surface which is obtained by taking a section through the measuring electrode in a plane normal to that of the measuring electrode. In accordance with this embodiment of the invention, the layers of the sandwich-like insulating body, in conjunction with an abutting metal lamina or with adjacent metal laminae, are constructed so as to form a trap for undesired diffusing substances.

Sputtering in a high-frequency field is a particularly well-suited procedure for forming the bodies and layers described herein since the requisite compactness and imperviousness of the bodies and layers are achievable by means of this procedure.

In particular, the output of the high-frequency field for the production of a metal layer is favorably between 10 and 40 watts per square centimeter of target surface. The target used in a particular instance should be composed of the same metal as that which is being sputtered. The sputtering is advantageously carried out in a gas atmosphere having a pressure of $8 \times 10^{-4}$ torr Ar for a period of 5 to 10 minutes.

For the production of $Al_2O_3$ and $SiO_2$ layers, the output of the high-frequency field is favorably between 30 and 50 watts per square centimeter of target surface. The target used should be composed of $Al_2O_3$ or $SiO_2$. The sputtering is advantageously carried out in a gas atmosphere having partial pressures of $3 \times 10^{-4}$ torr $O_2$ and $5 \times 10^{-4}$ torr Ar for a period of about 30 minutes.

For the production of $Si_3N_4$ layers, the output of the high-frequency field is favorably between 30 and 50 watts per square centimeter of target surface. The target used should be composed of $Si_3N_4$. The sputtering is favorably carried out in a gas atmosphere having partial pressures of $3 \times 10^{-4}$ torr $N_2$ and $5 \times 10^{-4}$ torr Ar for a period of about 30 minutes.

Under the conditions described above for the deposition of insulating materials, a reaction takes place between the target material in the gas phase and the deposit so that insulating layers of very dense or impervious construction are formed on the substrate or carrier. In this manner, it is also possible to deposit layers of other nonconducting compounds when the sum of the partial pressures of the reactive gas and the protective or carrier gas gives a total pressure of $8 \times 10^{-4}$ torr.

The high-frequency sputtering technique also makes it possible to deposit ion-sensitive glass layers with adequate precision and without a loss of the ion-sensitivity. This may be accomplished with a target of the ion-sensitive glass using a high-frequency field at an output of 10 to 40 watts per square centimeter of target surface. The sputtering is advantageously carried out in a gas atmosphere having partial pressures of $3 \times 10^{-4}$ torr $O_2$ and $5 \times 10^{-4}$ torr Ar for a period of 1 to 2 hours.

According to a favorable embodiment of the method according to the invention, the substrate or carrier is heated during the sputtering operation. When sputtering onto ion-sensitive glass, the temperature to which the substrate is heated is preferably maintained below about 80° C.

Hydrophobic layers are advantageously applied by means of a glow discharge.

If the substrate is in the form of a glass capillary, then the manufacturing operation may be facilitated by connecting or associating the glass capillary with a photoconductor. In this manner, the capillary is illuminated and the requisite manipulations such as grinding, forming and masking may be performed under optical control. According to one embodiment of the invention, that end of the glass capillary which is remote from the tip of the measuring device is connected with the photoconductor.

Referring now to the drawings, it is pointed out that, for a better understanding of the overall environment for the invention, FIG. 1 illustrates the invention, by way of example, as being embodied in a microprobe for ionic measurements.

The microprobe of FIG. 1 includes a coaxial cable A provided with outer insulation B and an electrical screen or shield C. The coaxial cable A includes copper wires E which are insulated with polyethylene. The coaxial cable A is cast or set in a Teflon sleeve F by means of pitch G. A lead glass tube I is connected with the cable A via Araldit H.

A Pt wire K is connected with the copper wires E via a joint J which might, for example, be in the form of a soldered or brazed joint. In order to achieve better contact, the Pt wire K is configured to act as a coil spring. The Pt wire K has a diameter of 100 micrometers.

The Pt wire K has a linear extension M which passes through a mass of $CaCl_2$ granulate into a drawn out or reduced capillaru portion N of the tube I. The extension or end M of the Pt wire, which has been electrolytically etched using an alternating current potential source, is tightly fused into the lead glass capillary portion N of the tube I in such a manner that no gaps exist between the extension M and the capillary portion N. The $CaCl_2$ granulate serves as a dessicant or drying agent.

The tip S of the microprobe is provided with measuring surfaces. Enlarged views of the latter are presented in FIGS. 2 and 3 which represent different sections through the tip S of the microprobe.

Figure 2:
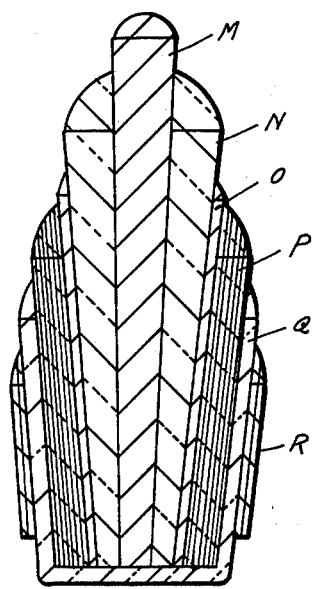
FIG. 2 represents a section through the tip of the microprobe of FIG. 1.

FIG. 2 shows a measuring surface which extends approximately normal to the axis of the microprobe and consequently has an approximately circular cross-section.

Figure 3:
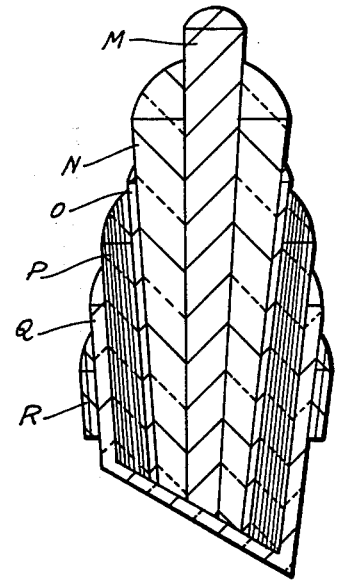
FIG. 3 represents a different section through the tip of the microprobe of FIG. 1.

FIG. 3 shows a measuring surface which is inclined to the axis of the microprobe and consequently has an ellipsoidal configuration.

In FIGS. 2 and 3, M again represents a section of Pt wire which has been electrolytically etched using a source of alternating current whereas N again represents the portion of the lead glass tube I which has been drawn out into the form of a capillary. O identifies an intermediate layer of Ta whereas P identifies a multilayered insulating body which, as seen in a direction from the inside towards the outside of the microprobe, consists of the layers $Al_2O_3$, $Si_3N_4$, $SiO_2$, $Ta_2N$ and $Ta_2O_5$, that is, the body P has the configuration $Al_2O_3$—$Si_3N_4$—$SiO_2$—$Ta_2N$—$Ta_2O_5$. Q represents a sputtered, ion-sensitive glass layer while R represents a multilayered metal-containing body which, as seen in a direction from the inside towards the outside of the microprobe, consists of a Ta inner layer, a Pt intermediate layer and a galvanically chlorinated Ag layer. A metal-containing body such as the body R may serve for the purpose of electrical shielding or screening and may also serve as a reference electrode.

It is noted that the constructions and/or compositions of the insulating and metal-containing bodies may depart from the exemplary constructions and compositions described herein if the conditions under which the measurements are taken should require such departures. However, the preceding and following exemplary constructions and compositions represent advantageous arrangements which are particularly well-suited for the measuring problems which normally arise.

For ease of description, the reference numerals and characters which are used to identify the various components in FIGS. 4–11 will be summarized here in the form of a list:

| | |
|---|---|
| 1 | internal buffer medium or solution |
| Z | body of insulating material; insulating layer; insulating packet |
| U | metal-containing body which includes a metal layer; metal-containing packet which includes a metal layer; metal layer |
| 4 | gaspermeable membrane |
| 5 | hydrophobic film or layer |
| 6 | electrolyte |
| 21 | multilayered insulator |
| 22 | intermediate or transition body or layer |
| 31 | metal packet having the configuration (Ta-Pt-Au-Pt-Ta) |
| 32 | metal-containing packet having the configuration (Ta-Pt-Ag-AgCl) |
| 33 | metal packet having the configuration (Ta-Pt-Ta) + (Pd) |
| 34 | metal packet having the configuration (Ta-Pt-Ta) |
| 35 | metal-containing packet having the configuration {[(Ta-Pt-Ta) + (Ag)]-[AgCl]} + {AgCl} |
| 36 | metal-containing packet having the configuration [Ta-Pt-TA] + [(Ag) + (AgCl)] |
| 101 | sputtered $pH^+$ ion-sensitive glass layer |
| 102 | sputtered $pNa^+$ ion-sensitive glass layer |
| 103 | sputtered $pK^+$ ion-sensitive glass layer |
| 201 | $Ta_2O_5$ layer |
| 202 | $Ta_2N$ layer |
| 203 | $Al_2O_3$ layer |
| 204 | $Si_3N_4$ layer |
| 205 | $SiO_2$ layer |
| 301 | Ta layer |
| 302 | Pt layer |
| 303 | Au layer |
| 304 | Ag layer |
| 1001 | ion-sensitive glass in bulk form |
| 1002 | lead glass in bulk form |
| 1003 | lead-free, highly insulating sealing or fusion glass |
| 3001 | galvanized Pd black |
| 3021 | bulk Pt in the form of wire having a diameter of about 200 micrometers |
| 3022 | bulk Pt in the form of wire having a diameter of about 100 micrometers |
| 3023 | Pt in bulk form which has been electrolytically etched using an alternating current source |
| 3031 | Au galvanized for strength |
| 3041 | Ag galvanized for strength |
| 3052 | galvanized AgCl |
| 3053 | electrode of galvanized AgCl |

The foregoing symbols will be used in the appended claims as well as in the description which follows.

It is again mentioned that, although the term "glass" is herein used in addition to terms such as "insulating material" and "insulator", this is not intended to imply that terms such as "insulating material" and "insulator" do not encompass glass.

Figure 4:
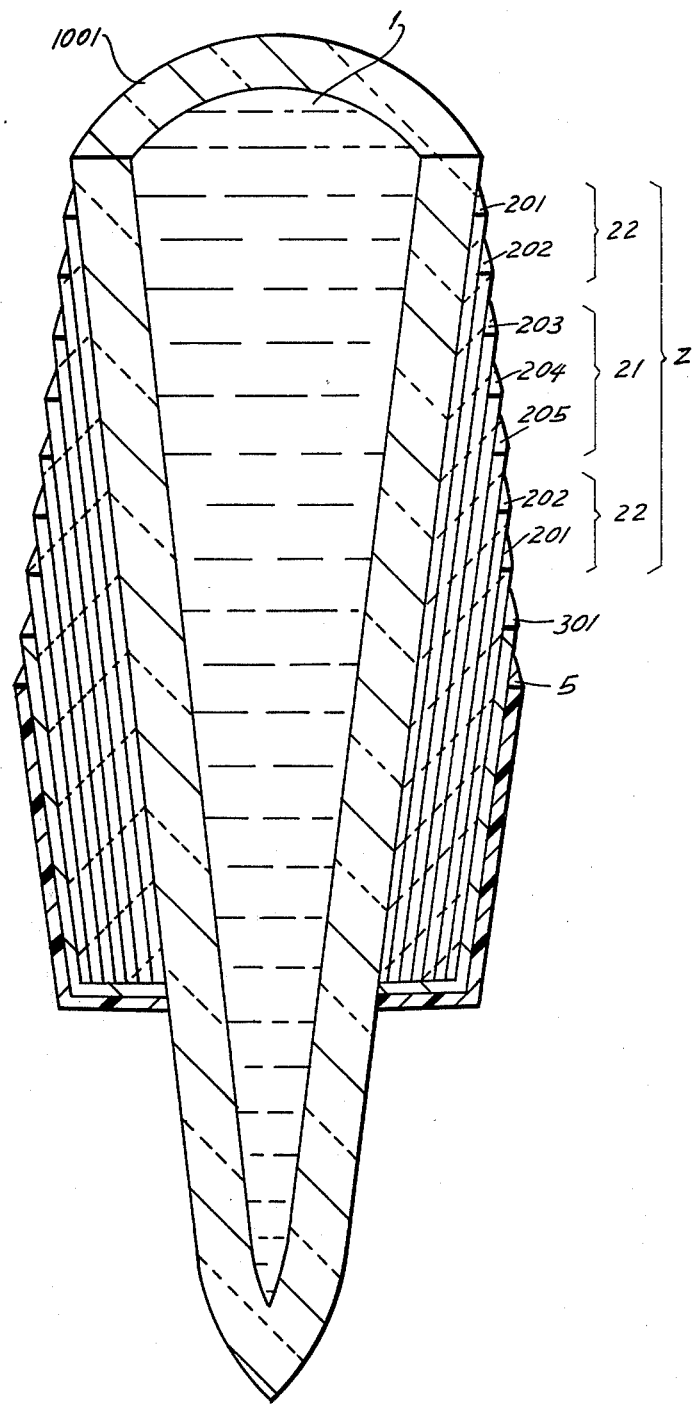
FIG. 4 represents a section through the tip of an ion-sensitive glass electrode which accommodates a buffer medium.

Referring now to FIG. 4 of the drawing, it may be seen that this illustrates an insulating body Z which is arranged on a substrate or carrier of ion-sensitive glass 1001. The insulating body Z, which is here shown as being in the form of an insulating packet, is made up of a multilayered insulator 21 which is arranged between a pair of transition bodies 22. The multilayered insulator 21 consists of a layer of $Al_2O_3$ identified by reference numeral 203, a layer of $Si_3N_4$ identified by reference numeral 204 and a layer of $SiO_2$ identified by reference numeral 205. The transition bodies 22 are each made up of a layer of $Ta_2O_5$ identified by the reference numeral 201 and a layer of $Ta_2N$ identified by the reference numeral 202.

A metal-containing body, which is here shown as being in the form of a Ta layer 301, is provided on the insulating packet Z. The metal-containing body need not be in the form of a Ta layer 301 and could, for instance, be in the form of a Ti layer or in the form of a metal-containing packet such as one having the configuration (Ta—Pt—Ta). The Ta layer 301 has been sputtered onto the insulating packet Z in a high-frequency field and thus completely seals the insulating packet against penetration by foreign matter.

A hydrophobic film 5, which may be applied by immersion or via a glow discharge, hinders attack of the underlying layers by water and concomitantly hinders the hydration resulting from such an attack.

By coating the ion-sensitive glass 1001 during sputtering in such a manner that, in the region of the end thereof, essentially only the tip of the ion-sensitive glass 1001 remains exposed, a small, very precisely defined field of measurement is obtained. The measuring device of FIG. 4 is suitable for the measurement of ionic activities.

The ion-sensitive glass 1001 is provided with an internal buffer 1. The configuration of the measuring device of FIG. 4 is thus $1-1001-\{[(Z-301)+(301)]-[5]+[5]\}$.

The coating of the ion-sensitive glass 1001 which is necessary for the manufacture of the measuring device may be facilitated from an optical viewpoint by connecting that end of the ion-sensitive glass 1001 which is opposite the end thereof provided with the measuring tip with a photoconductor. As a result, light rays will be emitted through the measuring tip which, in turn, causes the measuring tip to appear as a very bright point. This enables the requisite manipulations for the manufacture of the measuring device to be undertaken in a simple manner.

Figure 5:
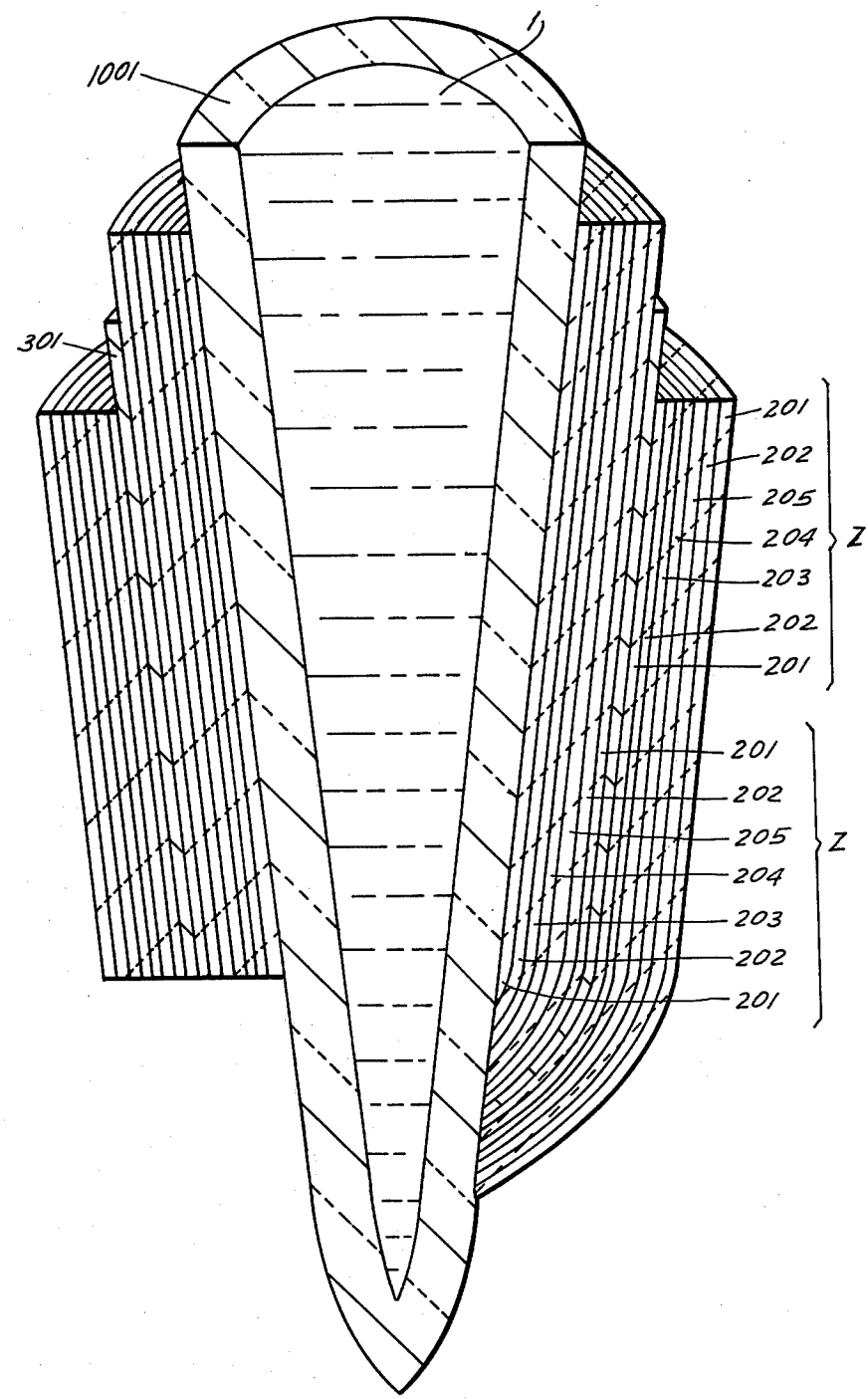
FIG. 5 represents a section through the tip of a glass electrode which is filled with a buffer solution and is provided with a sealing packet.

Referring now to FIG. 5, it may be seen that insulating packet Z and Ta layer 301 of FIG. 4 have been replaced with an expanded construction in the form of a sealing packet $Z-301-Z$. The configuration of the sealing packet $Z-301-Z$ of FIG. 5 is derived from the configuration $Z-301$ of FIG. 4 in that an additional insulating packet has been provided and arranged on the Ta layer 301. The sealing packet $Z-301-Z$ may terminate in a blunt edge as shown on the left-hand side of FIG. 5 or, on the other hand, the layers of the sealing packet $Z-301-Z$ may abut against and terminate at the ion-sensitive glass 1001 as shown on the right-hand side of FIG. 5. The measuring device of FIG. 5, which has the configuration $1-1001-(Z-301-Z)$, is suitable for the measurement of ionic activities in aggressive aqueous solutions.

Figure 6:
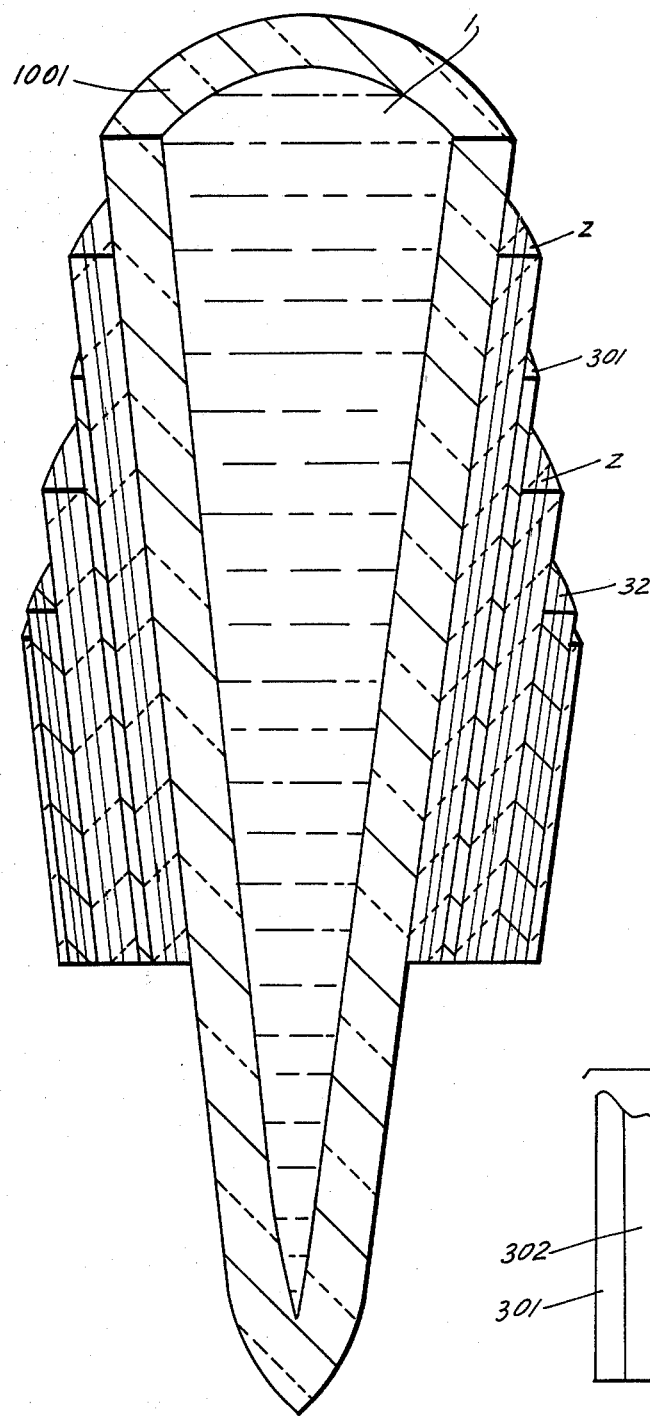
FIG. 6 represents a section through the tip of a glass electrode which is provided with a sealing packet and a reference electrode.
Figure 6A:
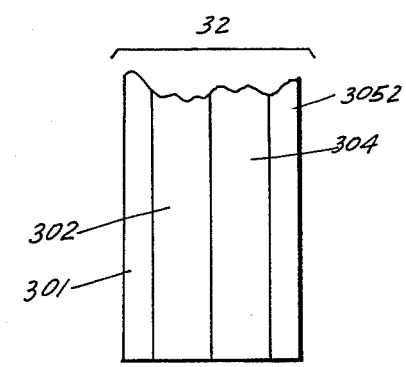
FIG. 6a represents an enlarged view of the reference electrode of FIG. 6.

FIG. 6 illustrates a measuring device which is provided with a reference electrode, in the form of a metal-containing packet 32, exteriorly of a sealing packet Z—301—Z. As clearly shown in FIG. 6a, the metal-containing packet 32 is constructed of a layer 301 of Ta, a layer 302 of Pt, a layer 304 of Ag and a layer 3052 of AgCl. Thus, the metal-containing packet 32 has the configuration 301—302—304—3052. The measuring device of FIG. 6, which has the configuration 1—1001—(Z—301—Z)—32=1—1001—(Z—301—Z)—(301—302—304—3052), is suitable for the measurement of ionic activities and for the measurement of $O_2$.

Figures 7, 7A:
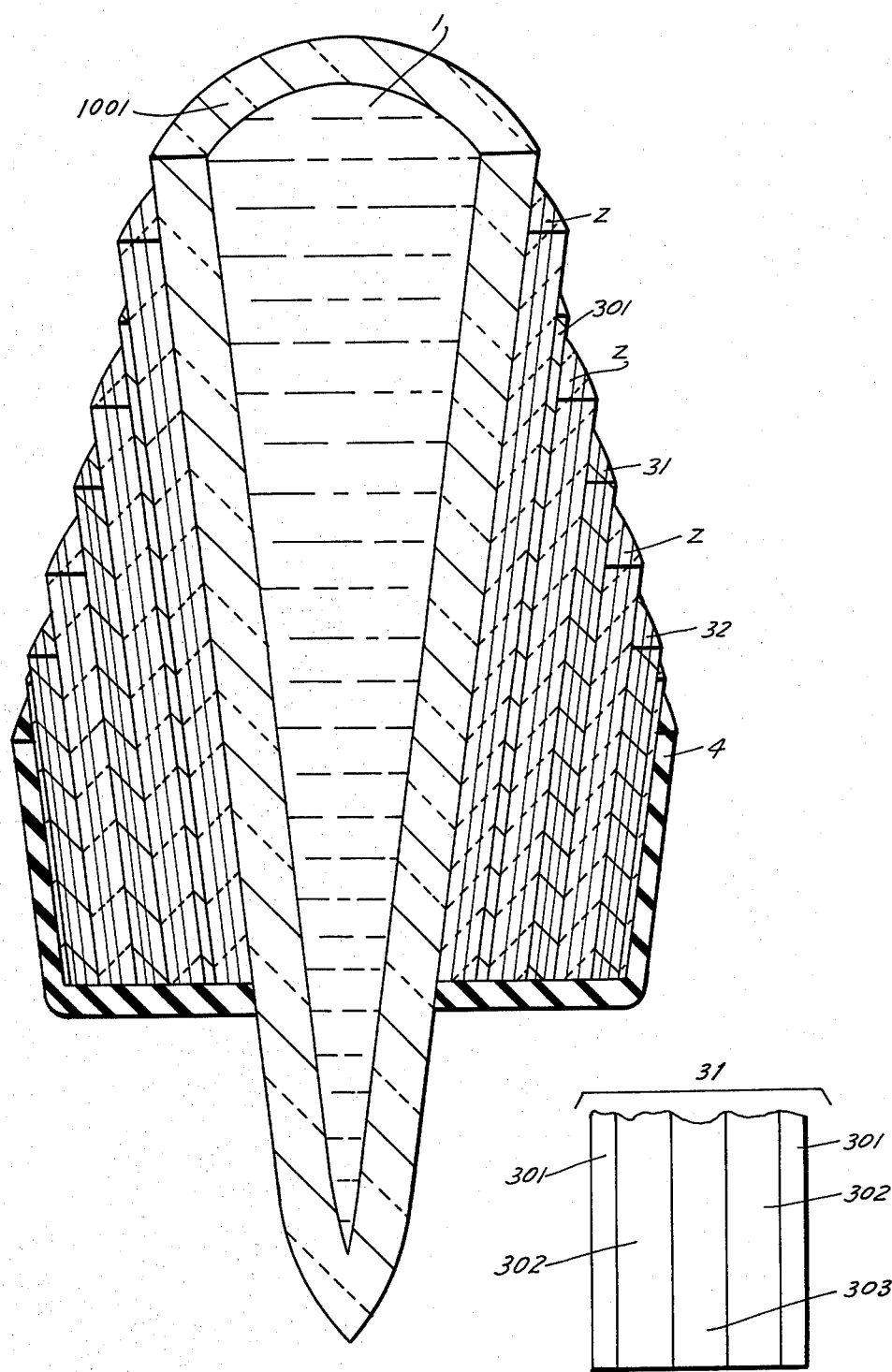
FIG. 7 represents a section through the tip of a glass electrode which is provided with a working electrode.
FIG. 7a represents an enlarged view of the working electrode of FIG. 7.

FIG. 7 illustrates a measuring device wherein a polarographic electrode, in the form of a metal packet 31, is provided on a sealing packet Z—301—Z. The metal packet 31 is made up of layers 301 of Ta, layers 302 of Pt and a layer 303 of Au as shown in FIG. 7a. The layers 301, 302 and 303 cooperate with one another and the configuration of the metal packet 31 is 301—302—303—302—301. An insulating packet Z is provided on the metal packet 31 and a reference electrode, in the form of the metal-containing packet 32, is provided on the latter insulating packet Z. A membrane 4, which is permeable to the gas that is to undergo measurement, is drawn over the entire layer construction. The configuration of the measuring device of FIG. 7 is thus 1—1001—{[(Z—301—Z)—31—Z—32]+[4]}—{4}. The measuring device is suitable for the simultaneous measurement of ionic activities and oxygen partial pressures.

Figures 8, 8A:
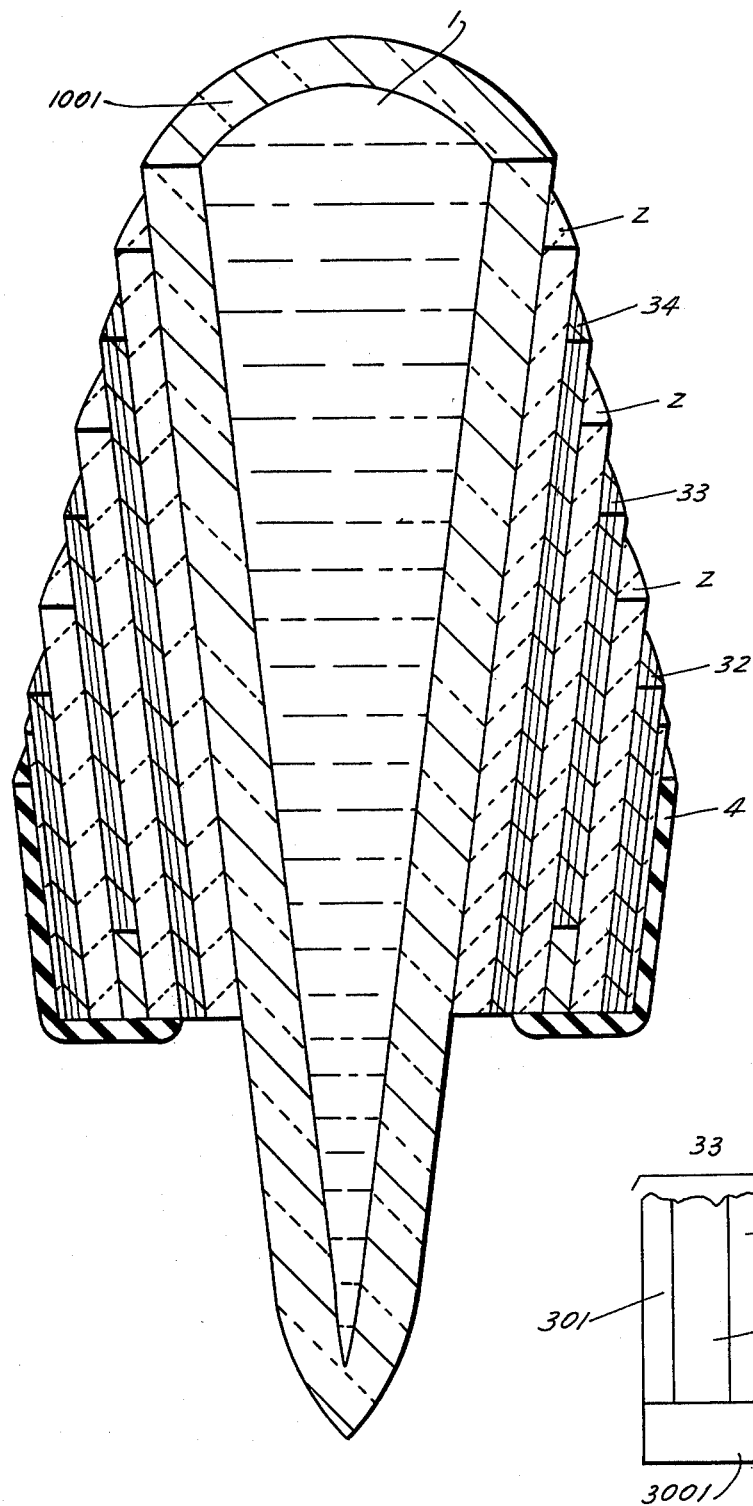
FIG. 8 represents a section through the tip of a glass electrode for the measurement of $H_2$ clearance with the simultaneous generation of $H_2$.
FIG. 8a represents an enlarged view of one of the coats provided on the glass electrode of FIG. 8.

In FIG. 8, a cone of ion-sensitive glass 1001 is coated with a body Z of insulating material on which there is arranged a working electrode in the form of a metal packet 34 consisting of Ta and Pt and having the configuration Ta—Pt—Ta. Another body Z of insulating material is arranged about the metal packet 34 and this latter body Z of insulating material is, in turn, coated with a metal packet 33. As clearly seen from FIG. 8a, the metal packet 33 is made up of layers 301 of Ta, a layer 302 of Pt and a layer of Pd black 3001, the latter layer being provided on the front or end face of the metal packet 33. The metal packet 33 thus has the configuration (301-302-301)+(3001). An additional body Z of insulating material is provided on the metal packet 33 and a reference electrode, in the form of the metal-containing packet 32, is, in turn, arranged about this additional body Z of insulating material. The memberane 4 is drawn over the layer construction provided on the ion-sensitive glass 1001 and covers the front or end face of the layer construction up to the working electrode 34. The measuring device of FIG. 8 has the configuration 1—1001—Z—34—[(Z—33—Z—32)+(4)]—[4]. With such a measuring device, it is possible to measure ionic activities and to simultaneously generate and measure $H_2$.

Figure 9:
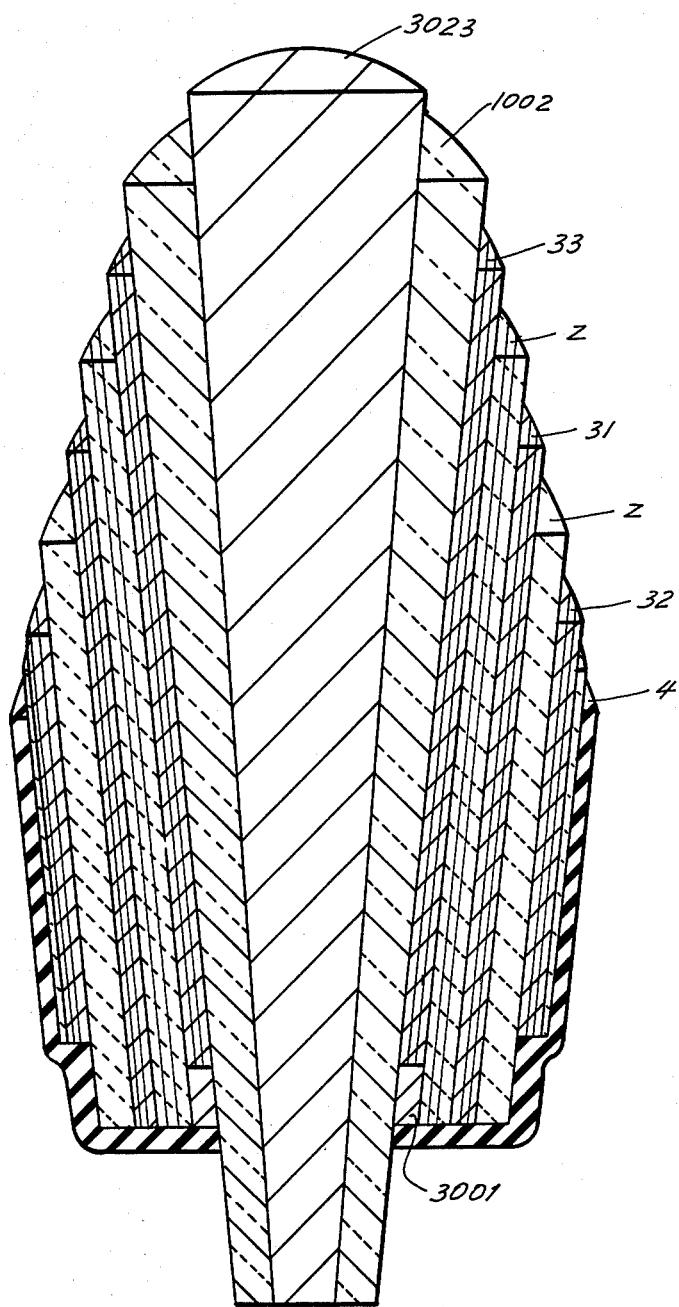
FIG. 9 represents a section through a Pt wire electrode for the punctiform generation of indicator gas and for the measurement of $H_2$ kinetics, ionic activities and $O_2$ partial pressures.

The measuring device of FIG. 9 includes a Pt wire 3023 which has been electrolytically etched to a diameter of less than 0.5 micrometer using an alternating current source. The Pt wire 3023 is fused into a coat of lead glass 1002 in such a manner that no gaps exist between the Pt wire 3023 and the lead glass 1002. The lead glass 1002 is coated with the metal packet 33 on the front or end face of which there is provided the layer of the Pd black 3001. A body Z of insulating material is arranged about the metal packet 33. In turn, the metal packet 31 is arranged about the body Z of insulating material whereas another body Z of insulting material is provided on the metal packet 31. The metal-containing packet 32 is arranged about the latter body Z of insulating material. The gas-permeable membrane 4 is drawn over the three outer electrodes, namely, the metal-containing packet 32, the metal packet 31 and the metal packet 33, of the measuring device, that is, the membrane 4 covers the front or end faces of the three outer electrodes of the measuring device.

The Pt wire of the measuring device of FIG. 9 can be used to generate $H_2$ which may then be measured by means of the metal packet 33. Simultaneously, the partial pressure of oxygen may be measured with the metal packet 31 using the metal-containing packet 32 as a reference electrode. The measuring device of FIG. 9 has the configuration 3023—1002—{[(33)+(3001]—[Z—31—Z—32]+[4]}—{4}.

Figure 10:
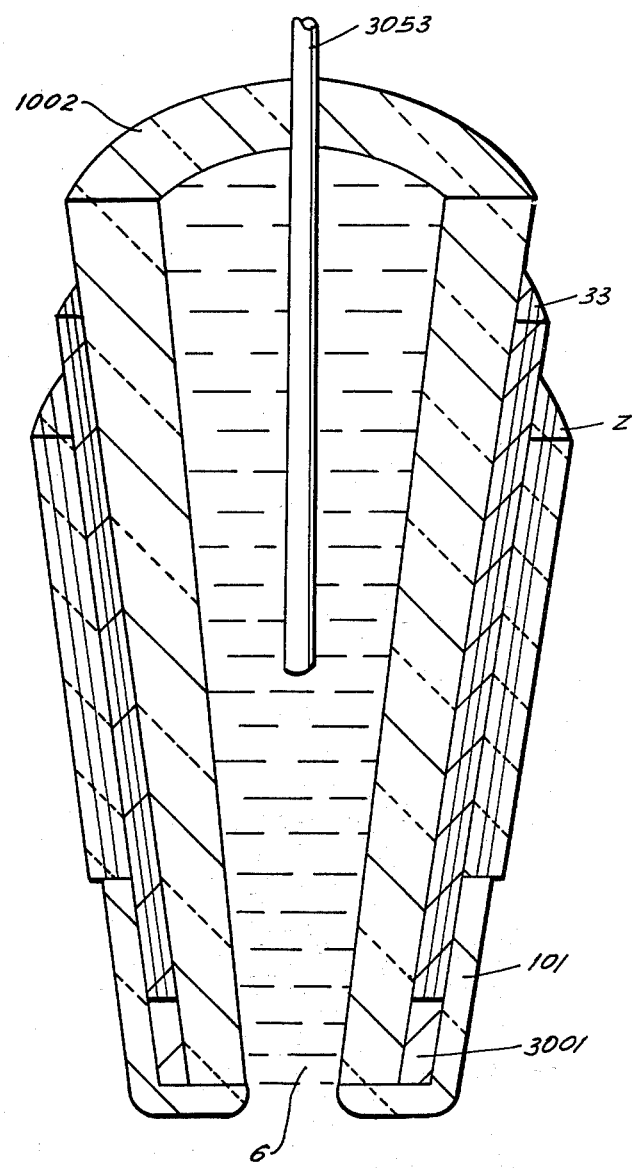
FIG. 10 represents a section through the tip of an ion-sensitive measuring electrode provided with sputtered layers and accommodating an electrolyte with a reference electrode.

FIG. 10 illustrates an arrangement which includes a capillary of lead glass 1002 filled with an electrolyte 6. An AgCl electrode 3053, which serves as a reference electrode, dips into the electrolyte 6. The metal packet 33, which serves as a shunt electrode, is provided on the capillary of lead glass 1002 and is in contact with a sputtered, $pH^+$-type ion-sensitive glass layer 101. In addition to the ion-sensitive glass layer 101, a body Z of insulating material is provided on the metal packet 33 and the body Z of insulating material bounds the ion-sensitive glass layer 101 so that the extent of the latter is restricted to a small cylindrical measuring area. The measuring device of FIG. 10, which has the configuration 6—[(1002—33)+(101)]—[(Z)+(101)], is capable of measuring ionic activities at biological membranes, for instance. It is pointed out that sputtered, $pNa^+$-type ion-sensitive glass layers 102 and sputtered, $pk^+$-type ion-sensitive glass layers 103 may also be used in the measuring device of FIG. 10.

The measuring device of FIG. 11 includes a plurality of Pt wires 3021 and 3022 which are embedded in highly-insulating, lead-free sealing glass 1003. A metal-containing packet 36 is arranged about the glass-embedded Pt wires 3021 and 3022 while an insulating packet Z is provided on the metal-containing packet 36. A second metal-containing packet 36 is arranged about the insulating packet Z and an additional insulating packet Z is provided on the second metal-containing packet 36. A pair of semi-cylindrical metal-containing packets 35, which are insulated from one another, are arranged on the additional insulating packet Z.

As may be seen from FIG. 11a, the metal-containing packets 35 are composed of a layer 301 of Ta, a layer 302 of Pt, a layer of galvanized Ag 3041 and a layer of galvanized AgCl 3052. The metal-containing packets 35 have the configuration {[(301—302—3041)+(3041)]—[3052]}+{3052}.

As may be seen from FIG. 11b, the metal-containing packets 36 are composed of layers 301 of Ta, a layer 302 of Pt, a layer of galvanized Ag 3041 and a layer of galvanized AgCl 3052. The metal-containing packets 36 have the configuration [301—302—301]+[(3041)+(3052)].

Referring once more to FIG. 11, it may be seen that one of the Pt wires 3022 is provided with a layer 101 pf sputtered, $pH^+$-type ion-sensitive glass, another of the Pt wires 3022 is provided with a layer 102 of $pNa^+$-type ion-sensitive glass and another of the Pt wires 3022 is provided with a layer 103 of $pK^+$-type ion-sensitive glass. The provision of the layers 101, 102 and 103 of ion-sensitive glass on these three Pt wires 3022 makes it possible to measure $H^+$, $Na^+$ and $K^+$ ions and to generate and measure $H_2$ gas. It is possible to provide ion-sensitive metal oxides on the Pt wires 3022 instead of the layers 101, 102 and 103 of ion-sensitive glass.

As indicated in FIG. 11, a fourth one of the Pt wires 3022 is provided with a layer of galvanized Au 3031 while the remaining Pt wire 3022 is provided with a layer of Pd black 3001.

The entire arrangement of FIG. 11 is covered with the membrane 4 up to the centrally positioned Pt wire 3021 which constitutes a working electrode, that is, the membrane 4 covers the front or end face of the arrangement of FIG. 11 up to the central Pt wire 3021. The membrane 4 has not been illustrated in FIG. 11 for the sake of clarity.

The configuration of the measuring device of FIG. 11 is 3021−1003{[; (3022)+(3001)−1003; (3022)+(101)−1003; (3022)+(102)−1003; (3022)+(103)−1003; (3022)+(3031)−1003]−36 −Z−36−Z−(35;Z;35)}+{4}.

The formation of the layers of a measuring device is effected by sputtering in a high-frequency field and does not pose any particular difficulties when the indicated operational specifications and data are observed. The operational specifications and data are as follows:

For the production of $Al_2O_3$ and $SiO_2$ layers, an output of about 30 to 50 watts per square centimeter of target surface should be maintained using an $Al_2O_3$ target when sputtering $Al_2O_3$ and using an $SiO_2$ target when sputtering $SiO_2$. A gas atmosphere containing $O_2$ at a partial pressure of about $3 \times 10^{-4}$ torr and Ar at a partial pressure of about $5 \times 10^{-4}$ torr should be used and the sputtering operation should be carried out for a period of about 30 minutes.

For the production of $Si_3N_4$ layers, the conditions just outlined need be departed from only to the extent that the target should now be an $Si_3N_4$ target and that, in lieu of oxygen, the sputtering atmosphere should now contain nitrogen at the same pressure as that used for the oxygen.

The metals are sputtered using a high-frequency field at an output of about 10 to 40 watts per square centimeter of target surface, the sputtering being performed for a period of about 5 to 10 minutes in an atmosphere containing Ar at a pressure of about $8 \times 10^{-4}$ torr.

The ion-sensitive glasses are sputtered using a high-frequency field at an output of about 10 to 40 watts per square centimeter of target surface, the sputtering being performed for a period of about 1 to 2 hours in an atmosphere containing $O_2$ at a partial pressure of about $3 \times 10^{-4}$ torr and Ar at a partial pressure of about $5 \times 10^{-4}$ torr.

Materials other than those described may likewise be deposited to form layers for electrodes if the sum of the partial pressures of the reactive gas and the protective or carrier gas gives a total pressure of about $8 \times 10^{-4}$ torr.

The substrate or carrier may be heated to temperatures of about 250° to 300° C. during sputtering for metal and insulating layers. For ion-sensitive substrates or carriers, the temperature should not be raised beyond about 80° C. The heating of the substrate or carrier results in very compact, impervious and adherent layers.

A hydrophobic layer may be applied to a measuring device according to the invention. The hydrophobic layer, which is favorably composed of a polytitanosiloxane, may be applied by immersion or by means of a glow discharge in vacuum.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A measuring device for use in biologic systems, including a probe having a body of insulating material and a conductive coat applied on said body to delineate a measuring area thereon, said coat comprising at least one layer of a metal selected from the group consisting of Ta, Pt, Au, Ag, Pd and Al and deposited on said body by a sputtering process performed in a high frequency field at an output of about 10-40 watts per square centimeter of metal target surface for a period of about 5-10 minutes in an atmosphere having an Ar pressure of about $8 \times 10^{-4}$ torr.

2. A device as defined in claim 1, comprising a layer of insulating material arranged about said coat.

3. A device as defined in claim 1, wherein said metal layer consists essentially of Ta.

4. A device as defined in claim 1, wherein said coat comprises a plurality of pore-free metal layers at least one of which is composed of a metal different from that of another of said metal layers.

5. A device as defined in claim 4, wherein said coat has the configuration (Ta−Pt−Au−Pt−Ta) and:
"−" represents travel in radially outward direction.

6. A device as defined in claim 4, wherein said coat has the configuration (Ta−Pt−Ag−AgCl) and:
"−" represents travel in radially outward direction.

7. A device as defined in claim 6, wherein the Ta layer of said coat is adjacent said insulating material.

8. A device as defined in claim 4, wherein said coat has the configuration (Ta−Pt−Ta)+(Pd) and:
"−" represents travel in radially outward direction, and
"−" represents travel in axial direction towards a measuring surface.

9. A device as defined in claim 4, wherein said coat has the configuration (Ta−Pt−Ta) and:
"−" represents travel in radially outward direction.

10. A device as defined in claim 4, wherein said coat has the configuration {[(Ta−Pt−Ta)+(Ag)]−[AgCl]}+{AgCl} and:
"−" represents travel in radially outward direction, and
"+" represents travel in axial direction towards a measuring surface.

11. A device as defined in claim 4, wherein said coat has the configuration [Ta−Pt−Ta]+[(Ag)+(AgCl)] and:
"−" represents travel in radially outward direction, and
"+" represents travel in axial direction towards a measuring surface.

12. A device as defined in claim 1, comprising at least one intermediate body between said insulating material and said metal layer.

13. A device as defined in claim 12, wherein said intermediate body comprises a plurality said layers and has the configuration ($Ta_2N$-$Ta_2O_5$) and:
"−" represents travel in radially outward direction.

14. A device as defined in claim 13, said metal layer consisting essentially of Ta; and wherein the $Ta_2O_5$ layer of said intermediate body is adjacent said metal layer.

15. A device as defined in claim 1, wherein said body of insulating material comprises a plurality of layers and has the configuration ($Al_2O_3$—$Si_3N_4$—$SiO_2$) and:

"—" represents travel in radially outward direction.

16. A device as defined in claim 1, wherein said body of insulating material is arranged between a pair of additional bodies having insulating characteristics and said additional bodies and said body of insulating material together constitute an insulating packet.

17. A device as defined in claim 16, wherein each of said additional bodies comprises a layer of $Ta_2O_5$ and a layer of $Ta_2N$.

18. A device as defined in claim 16, said metal layer being arranged about said insulating packet; and wherein another insulating packet similar to the latter is arranged about said metal layer.

19. A device as defined in claim 18, wherein said metal layer and said insulating packets are arranged on a glass electrode so as to obtain the configuration E—(-Z—U—Z) for permitting the measurement of ions and:

"—" represents travel in radially outward direction,
E represents said glass electrode,
Z represents an insulating packet, and
U represents said metal layer.

20. A device as defined in claim 19, wherein said glass electrode comprises ion-sensitive glass.

21. A device as defined in claim 1, said body of insulating material and said metal layer being arranged on a glass electrode; and wherein a layer of hydrophobic material is arranged about said metal layer so as to obtain the configuration E—[(Z—U)+(5)]+[5] and:

"—" represents travel in radially outward direction,
"+" represents travel in axial direction towards a measuring surface,
E represents said glass electrode,
Z represents said insulating material,
U represents said metal layer, and
5 represents said layer of hydrophobic material.

22. A device as defined in claim 21, wherein said metal layer consists essentially of Ta and said glass electrode comprises ion-sensitive glass.

23. A device as defined in claim 1, said insulating material and said metal layer being arranged on a glass electrode; and wherein at least one additional metal-containing body and at least one additional body of insulating material are arranged on said glass electrode, and a gas-permeable membrane is arranged about said metal-containing and insulating bodies so as to obtain the configuration E—[(Z—U—Z—U—Z—U)+(4)]—[4] where:

"—" represents travel in radially outward direction,
"+" represents travel in axial direction towards a measuring surface,
E represents said glass electrode,
Z represents a body of insulating material,
U represents a metal-containing body which includes a metal layer, and
4 represents said gas-permeable membrane.

24. A device as defined in claim 23, wherein said configuration is 1001—[(Z—301—Z—31—Z—32)+(4)] —[4] so as to permit polarography to be carried out simultaneously with the measurement of ions and:

1001 represents a glass electrode which comprises ion-sensitive glass,
301 represents a metal layer consisting essentially of Ta,
31 represents a metal-containing packet having the configuration (Ta—Pt—Au—Pt—Ta), and
32 represents a metal-containing packet having the configuration (Ta—Pt—Ag—AgCl).

25. A device as defined in claim 1, comprising additional probes so as to obtain a multiple-electrode configuration, and additional bodies of insulating material separating said probes.

26. A device as defined in claim 25, wherein said probes are high-resistance glass electrodes.

27. A device as defined in claim 1, said metal layer being arranged on a glass electrode; and wherein at least one additional metal-containing body and at least one additional body of insulating material are arranged on said glass electrode, and a gas-permeable membrane is arranged about said metal-containing and insulating bodies so as to obtain the configuration E—Z—U—[(-Z—U—Z—U)+(4)]—[4] where:

"—" represents travel in radially outward direction,
"+" represents travel in axial direction towards a measuring surface,
E represents said glass electrode,
Z represents a body of insulating material,
U represents a metal-containing body which includes a metal layer, and
4 represents said gas-permeable membrane.

28. A device as defined in claim 27, wherein said configuration is 1001—Z—34—[(Z—33—Z—32)+(4)]—[4] so as to permit the measurement of ions and $H_2$ clearance with the simultaneous generation of $H_2$ and:

1001 represents a glass electrode which comprises ion-sensitive glass,
34 represents a metal-containing packet having the configuration (Ta—Pt—Ta),
33 represents a metal-containing packet having the configuration (Ta—Pt—Ta)+(Pd), and
32 represents a metal-containing packet having the configuration (Ta—Pt—Ag—AgCl).

29. A device as defined in claim 1, comprising a glass-embedded Pt wire; and wherein said insulating material and said metal layer, as well as at least one additional metal-containing body, at least one additional body of insulating material and a gas-permeable membrane, are arranged about said Pt wire so as to obtain the configuration W—G—[(U—Z—U—Z)+(4)]—[4] where:

"—" represents travel in radially outward direction,
"+" represents travel in axial direction towards a measuring surface,
W represents said Pt wire,
G represents the glass embedding said Pt wire,
U represents a metal-containing body which includes a metal layer,
Z represents a body of insulating material, and
4 represents said gas-permeable membrane.

30. A device as defined in claim 29, said Pt wire being fused into said glass; and wherein said configuration is 3023—1002—[(33—Z—31—Z)+(4)]—[4] so as to permit a quasipunctiform measurement of ions and hydrogen and:

3023 represents Pt wire which has been electrolytically etched using alternating current,
1002 represents lead glass,
33 represents a metal-containing packet having the configuration (Ta—Pt—Ta)+(Pd), and
31 represents a metal-containing packet having the configuration (Ta—Pt—Au—Pt—Ta).

31. A device as defined in claim 1, comprising five Pt wires which are at least partially embedded in glass; and wherein said insulating material and said metal layer, as well as at least one additional metal-containing body, at least one additional body of insulating material and a gas-permeable membrane, are arranged about said Pt wires so as to obtain the configuration W−G{(;(W)+(G)−G; (W)+(G)−G; (W)+(G)−G; (W)+(U)−G)−U−Z−U−Z−(U;Z;U)}+{4} where:
"−" represents travel in radially outward direction,
"+" represents travel in axial direction towards a measuring surface,
";" represents travel in tangential direction,
W represents a Pt wire,
G represents glass,
U represents a metal-containing body which includes a metal layer,
Z represents a body of insulating material, and
4 represents said gas-permeable membrane.

32. A device as defined in claim 31, wherein said configuration is 3021−1003{(;(3022)+(101) −1003; (3022)+(102)−1003; (3022)+(103)−1003; (3022)+(3031)−1003)−36−Z−36−Z−(35;Z;35)}+-{4} so as to permit the measurement of ions, hydrogen and oxygen with the simultaneous generation of hydrogen and:
3021 represents a Pt wire having a diameter of approximately 200 micrometers,
1003 represents substantially lead-free, highly insulating glass into which said Pt wires are fused,
3022 represents a Pt wire having a diameter of approximately 100 micrometers,
101 represents a pH$^+$-type, ion-sensitive, sputtered glass layer,
102 represents a pNa$^+$-type, ion-sensitive, sputtered glass layer,
103 represents a pK$^+$-type, ion-sensitive, sputtered glass layer,
3031 represents Au which has been galvanized for increased strength,
36 represents a metal-containing packet having the configuration (Ta−Pt−Ta)+(Ag)+(AgCl), and
35 represents a metal-containing packet having the configuration {[(Ta−Pt−Ta)+(Ag)]−[AgCl]}-+{AgCl}.

33. A device as defined in claim 1, comprising a glass capillary having an opening adapted to face a substance which is to be subjected to a measurement, an electrolyte in said glass capillary and a reference electrode in said electrolyte; and wherein said metal layer, as well as a glass layer, are arranged about said glass capillary so as to obtain the configuration E−6−(G−U)+(G)−Z for permitting measurements in small cylindrical measuring zones and:
"−" represents travel in radially outward direction,
"+" represents travel in axial direction towards a measuring surface,
E represents said reference electrode,
6 represents said electrolyte,
G represents glass,
U represents a metal-containing body which includes a metal layer, and
Z represents a body of insulating material.

34. A device as defined in claim 33, wherein said configuration is 3053−6−(1002−33)+(101)−Z and:
3053 represents a galvanized AgCl electrode,
1002 represents lead glass,
33 represents a metal-containing packet having the configuration (Ta−Pt−Ta)+(Pd), and
101 represents a pH$^+$-type, ion-sensitive, sputtered glass layer.

35. A device as defined in claim 1, comprising a hydrophobic layer arranged about said metal layer in such a manner that at least a portion of said probe is not covered by said hydrophobic layer.

36. A device as defined in claim 35, wherein said hydrophobic layer comprises a polytitanosiloxane.

37. A device as defined in claim 1, comprising an insulating carrier, a measuring electrode, a working surface and a membrane for protecting said working surface against contamination; and wherein said body of insulating material comprises a plurality of thin films composed of different insulating materials and arranged in a sandwich-like fashion and in an alternating array, said measuring electrode being in the form of a thin film having noble metal properties and being arranged intermediate said insulating carrier and said body of insulating material, and said thin films of said body of insulating material cooperating with at least one metal lamina which abuts said body of insulating material to form a trap for undesired diffusing substances, said working surface being in the form of a surface which is obtained by taking a section through said measuring electrode in a plane arranged substantially normal to the plane of said measuring electrode, and said device permitting the polarographic determination of the partial pressures of gases such as oxygen in aqueous solutions such as biological media.

38. A device as defined in claim 37, wherein said measuring electrode comprises a noble metal.

39. A device as defined in claim 37, wherein said measuring electrode comprises a metallic alloy having noble metal properties.

40. A method of forming a probe for use in biologic systems and including a conductive layer on an insulating substrate, comprising forming said layer by sputtering a metal selected from the group consisting of Ta, Pt, Au, Ag, Pd and Al onto said substrate using a high-frequency field at an output of about 10 to 40 watts per square centimeter of target surface, said sputtering being performed with a target of said metal, and said sputtering being carried out for a period of about 5 to 10 minutes in an atmosphere having an Ar pressure of about $8 \times 10^{-4}$ torr.

41. A method as defined in claim 40, wherein the total pressure of said atmosphere is about $8 \times 10^{-4}$ torr.

42. A method as defined in claim 40, wherein said substrate is heated during said sputtering.

43. A method as defined in claim 42, wherein said substrate comprises ion-sensitive glass and is heated to temperatures less than about 80° C.

44. A method as defined in claim 40, wherein treatment of said substrate is facilitated by connecting said substrate with a photoconductor which illuminates said substrate.

45. A method as defined in claim 44, said substrate comprising glass, and said substrate being used as a component in a measuring device which includes a high-resistance transducer, an insulating material arranged about said transducer and at least one substantially closed metal layer which is resistant to the diffusion of liquid therethrough arranged about said insulating material; and wherein said substrate has a tip provided with a measuring surface for said measuring device and an end which is remote from said tip, said end of said substrate being connected with said photoconductor.

46. A method as defined in claim 45, wherein said measuring device is provided with a layer of hydrophobic material by means of a glow discharge.

47. A method as defined in claim 40, wherein the metal-coated substrate is used as a component in a measuring device which includes a high-resistance transducer, an insulating material arranged about said transducer and at least one substantially closed metal layer which is resistant to the diffusion of liquid therethrough arranged about said insulating material.

48. A method as defined in claim 40; and further comprising the step of forming a layer of insulating material on said substrate by depositing said insulating material on said substrate in an atmosphere which includes protective gas and reactive gas having partial pressures such that the sum thereof is of the order of $8 \times 10^{-4}$ torr.

49. A method as defined in claim 48, wherein the total pressure in said atmosphere is about $8 \times 10^{-4}$ torr.

50. A method as defined in claim 48, wherein said insulating material is sputtered onto said substrate.

51. A method as defined in claim 48, wherein said substrate is heated during said deposition.

52. A method as defined in claim 51, wherein said substrate comprises ion-sensitive glass and is heated to temperatures less than about 80° C.

53. A method as defined in claim 48, wherein treatment of said substrate is facilitated by connecting said substrate with a photoconductor which illuminates said substrate.

54. A method as defined in claim 53, said substrate comprising glass, and said substrate being used as a component in a measuring device which includes a high-resistance transducer, an insulating material arranged about said transducer and at least one substantially closed metal layer which is resistant to the diffusion of liquid therethrough arranged about the latter insulating material; and wherein said substrate has a tip provided with a measuring surface for said measuring device and an end which is remote from said tip, said end of said substrate being connected with said photoconductor.

55. A method as defined in claim 54, wherein said measuring device is provided with a layer of hydrophobic material by means of a glow discharge.

56. A method as defined in claim 48, said insulating material being a member of the group consisting of $Al_2O_3$ and $SiO_2$; and wherein said deposition comprises sputtering said insulating material onto said substrate using a target from the group consisting of $Al_2O_3$ and $SiO_2$, said sputtering being performed using a high-frequency field at an output of about 30 to 50 watts per square centimeter of target surface, and said sputtering being carried out for a period of about 30 minutes in an atmosphere which includes $O_2$ at a pressure of about $3 \times 10^{-4}$ torr and Ar at a pressure of about $5 \times 10^{-4}$ torr.

57. A method as defined in claim 48, said insulating material being $Si_3N_4$; and wherein said deposition comprises sputtering said insulating material onto said substrate using an $Si_3N_4$ target, said sputtering being performed using a high-frequency field at an output of about 30 to 50 watts per square centimeter of target surface, and said sputtering being carried out for a period of about 30 minutes in an atmosphere which includes $N_2$ at a pressure of about $3 \times 10^{-4}$ torr and Ar at a pressure of about $5 \times 10^{-4}$ torr.

58. A method as defined in claim 48, said insulating material being ion-sensitive glass; and wherein said deposition comprises sputtering said insulating material onto said substrate using a target of said ion-sensitive glass, said sputtering being performed using a high-frequency field at an output of about 10 to 40 watts per square centimeter of target surface, and said sputtering being carried out for a period of about 1 to 2 hours in an atmosphere which includes $O_2$ at a pressure of about $3 \times 10^{-4}$ torr and Ar at a pressure of about $5 \times 10^{-4}$ torr.

59. A method as defined in claim 48, wherein the insulator-coated substance is used as a component in a measuring device which includes a high-resistance transducer, an insulating material arranged about said transducer and at least one substantially closed metal layer which is resistant to the diffusion of liquid therethrough arranged about said insulating material.

* * * * *